(12) United States Patent
Takemoto et al.

(10) Patent No.: US 10,881,275 B2
(45) Date of Patent: Jan. 5, 2021

(54) MEDICAL DEVICE INSERTION METHOD

(71) Applicant: OLYMPUS CORPORATION, Tokyo (JP)

(72) Inventors: Shotaro Takemoto, Tokyo (JP); Takeshi Murata, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 299 days.

(21) Appl. No.: 16/053,863

(22) Filed: Aug. 3, 2018

(65) Prior Publication Data

US 2020/0037859 A1 Feb. 6, 2020

(51) Int. Cl.
*A61B 1/00* (2006.01)
*A61B 1/31* (2006.01)
*A61B 1/005* (2006.01)

(52) U.S. Cl.
CPC ........ *A61B 1/00135* (2013.01); *A61B 1/0057* (2013.01); *A61B 1/31* (2013.01)

(58) Field of Classification Search
None
See application file for complete search history.

(56) References Cited

U.S. PATENT DOCUMENTS 5,569,159 A * 10/1996 Anderson .......... A61B 1/00142
600/114
6,981,945 B1 * 1/2006 Sarvazyan ......... A61B 1/00147
600/131
2002/0147385 A1 * 10/2002 Butler ............... A61B 1/00137
600/114
2015/0005894 A1 1/2015 Nomura et al.
2017/0128188 A1 5/2017 Nomura et al.

FOREIGN PATENT DOCUMENTS

| EP | 2 965 723 A1 | 1/2016 |
| JP | S63-197503 U | 12/1988 |
| JP | H09-225036 A | 9/1997 |
| JP | 5642909 B | 12/2014 |
| JP | 2015-061548 A | 4/2015 |

* cited by examiner

*Primary Examiner* — Timothy J Neal
(74) *Attorney, Agent, or Firm* — Scully, Scott, Murphy & Presser, P.C.

(57) ABSTRACT

A medical device insertion method includes: inserting an endoscope into an overtube until a distal end of the endoscope protrudes from a distal end of the overtube; grasping a part of the endoscope protruding from the distal end of the overtube and inserting the endoscope into the large intestine until the distal end of the endoscope is between the splenic flexure and the sigmoid colon of the large intestine; and inserting the overtube together with the endoscope into the large intestine until the distal end of the endoscope is beyond the splenic flexure while grasping the overtube from an outer radial direction so as to deform the overtube in an inner radial direction until an inner surface of the overtube is pressed against an outer circumferential surface of the endoscope, and then inserting the overtube into the large intestine until a reinforced region is placed in the splenic flexure.

5 Claims, 11 Drawing Sheets

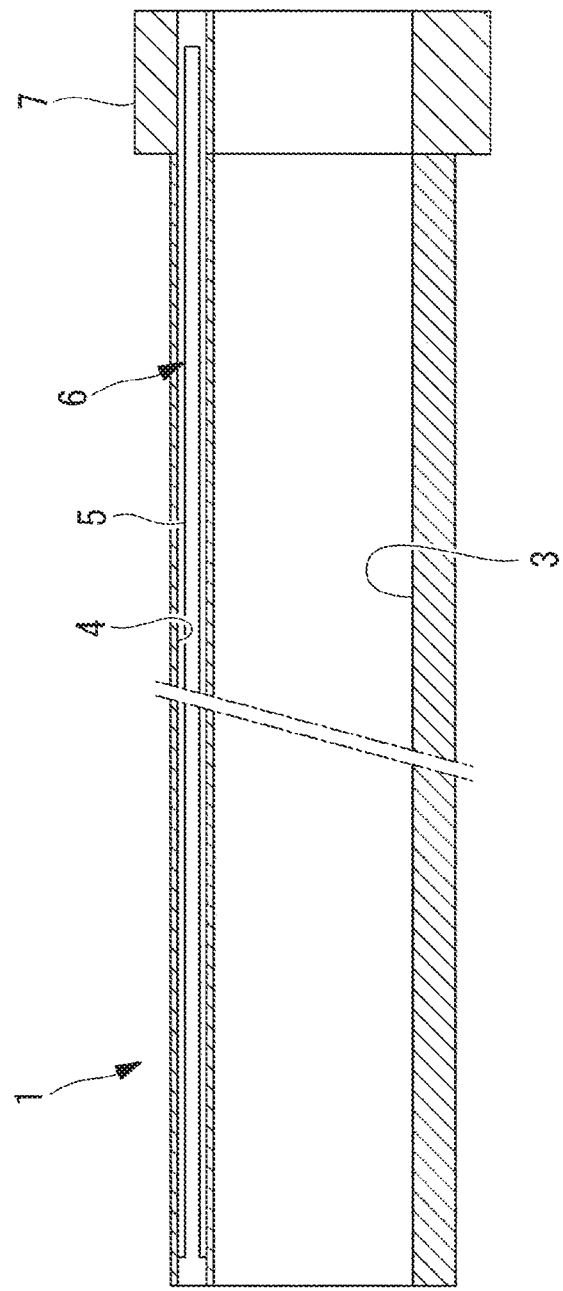

MEDICAL DEVICE INSERTION METHOD

TECHNICAL FIELD

The present invention relates to a medical device insertion method.

BACKGROUND ART

There is a known method for inserting an endoscope into the large intestine, with which the endoscope is housed in an overtube and is inserted into the large intestine together with the overtube (for example, refer to PTL 1).

CITATION LIST

Patent Literature

{PTL 1} Japanese Unexamined Utility Model Application, Publication No. 63-197503

SUMMARY OF INVENTION

Technical Problem

In starting the insertion from the anus toward the large intestine, in particular, in passing through the sigmoid colon, it is preferable to insert an endoscope first and then an overtube rather than inserting an endoscope and an overtube together.

However, the issue is that, when the endoscope is not sufficiently inserted into the large intestine, that is, when the distal end of the endoscope is on the anus side with respect to the splenic flexure of the large intestine, and when the operator takes his or her hands off the endoscope in order to insert the overtube after inserting the endoscope, the endoscope is pushed back and out from the anus.

An object of the present invention is to provide a medical device insertion method used in inserting an overtube after the insertion of an endoscope, with which the overtube can be inserted even when the endoscope is not sufficiently inserted into the large intestine.

Solution to Problem

According to one aspect, the present invention provides a medical device insertion method for inserting an overtube and an endoscope into the large intestine, the overtube including a reinforced region in at least one part in a longitudinal axis direction, the reinforced region including a wire disposed in at least one part of an outer circumference of the overtube and disposed along the longitudinal axis direction, the method including: inserting the endoscope into the overtube until a distal end of the endoscope is positioned to protrude from a distal end of the overtube; grasping a part of the endoscope protruding from the distal end of the overtube and inserting the endoscope into the large intestine until the distal end of the endoscope is positioned between the splenic flexure and the sigmoid colon of the large intestine; and inserting the overtube together with the endoscope into the large intestine until the distal end of the endoscope is placed beyond the splenic flexure while grasping the overtube from an outer radial direction so as to deform the overtube in an inner radial direction until an inner surface of the overtube is pressed against an outer circumferential surface of the endoscope, and then inserting the overtube into the large intestine until the reinforced region is placed in the splenic flexure.

According to this aspect, first, the endoscope is inserted into the overtube, and the endoscope protruding from the distal end of the overtube is grasped and is inserted until the distal end of the endoscope passes the sigmoid colon. In this manner, the endoscope can be inserted by directly applying force. Next, the endoscope is grasped and deformed by squashing the overtube from the outer side of the overtube, and the endoscope and the overtube are together inserted into the large intestine. In this manner, compared to the case in which the endoscope is grasped at the proximal end side with respect to the overtube while preventing the endoscope from being pushed out from the large intestine toward the anus side, the force can be applied to the endoscope at a position near the anus, and the operation of inserting the endoscope into the large intestine can be smoothly carried out.

Furthermore, after the distal end of the endoscope is placed beyond the splenic flexure, only the overtube is advanced by using the endoscope as a guide, and thus the reinforced region formed in at least one part of the overtube in the longitudinal axis direction can be placed in the splenic flexure. As a result, even when only the endoscope is removed thereafter, the endoscope can be easily re-inserted by using the overtube as a guide.

In the aspect described above, after only the endoscope is removed from the overtube, which has the reinforced region placed in the splenic flexure, so as to leave the overtube in the large intestine, the overtube may be rotated about the longitudinal axis so as to resolve collapse of an inner hole of the overtube in the splenic flexure, and subsequently, the endoscope may be protruded from the distal end of the overtube.

With this structure, when the overtube is left in the large intestine by removing only the endoscope, the inner hole of the overtube may collapse in the splenic flexure where the overtube is sharply bent in the large intestine. In such a case also, since the reinforced region is disposed in the splenic flexure, the collapse of the inner hole can be resolved by rotating the overtube about the longitudinal axis to move the wire in the circumferential direction before re-insertion of the endoscope, and the subsequent re-insertion operation can be smoothly carried out.

In the aspect described above, the wire may be placed on an inner side of the bend of the splenic flexure by rotating the overtube about the longitudinal axis.

With this structure, when the wire is placed on the inner side of the bend of the splenic flexure by rotating the overtube, the wall of the collapsed overtube is stretched, and the collapse of the inner hole can be easily resolved.

In the aspect described above, before rotating the overtube, the endoscope may be inserted to a position on the sigmoid colon side with respect to the splenic flexure, and a deformed state of the inner hole of the overtube in the splenic flexure may be checked with the endoscope.

With this structure, the deformed state of the inner hole of the overtube in the splenic flexure can be easily checked with the endoscope, and the overtube rotation direction and the overtube rotation angle needed to resolve the collapse of the inner hole can be predicted. Thus, the collapse of the inner hole can be more efficiently resolved.

Advantageous Effects of Invention

The present invention has an advantageous effect in that, in inserting an overtube after the insertion of an endoscope, the overtube can be inserted even when the endoscope is not sufficiently inserted into the large intestine.

BRIEF DESCRIPTION OF DRAWINGS

FIG. 12 is a longitudinal sectional view of a modification of the overtube illustrated in FIG. 1.

DESCRIPTION OF EMBODIMENTS

The medical device insertion method according to one embodiment of the present invention will now be described with reference to the drawings.

Figure 1:
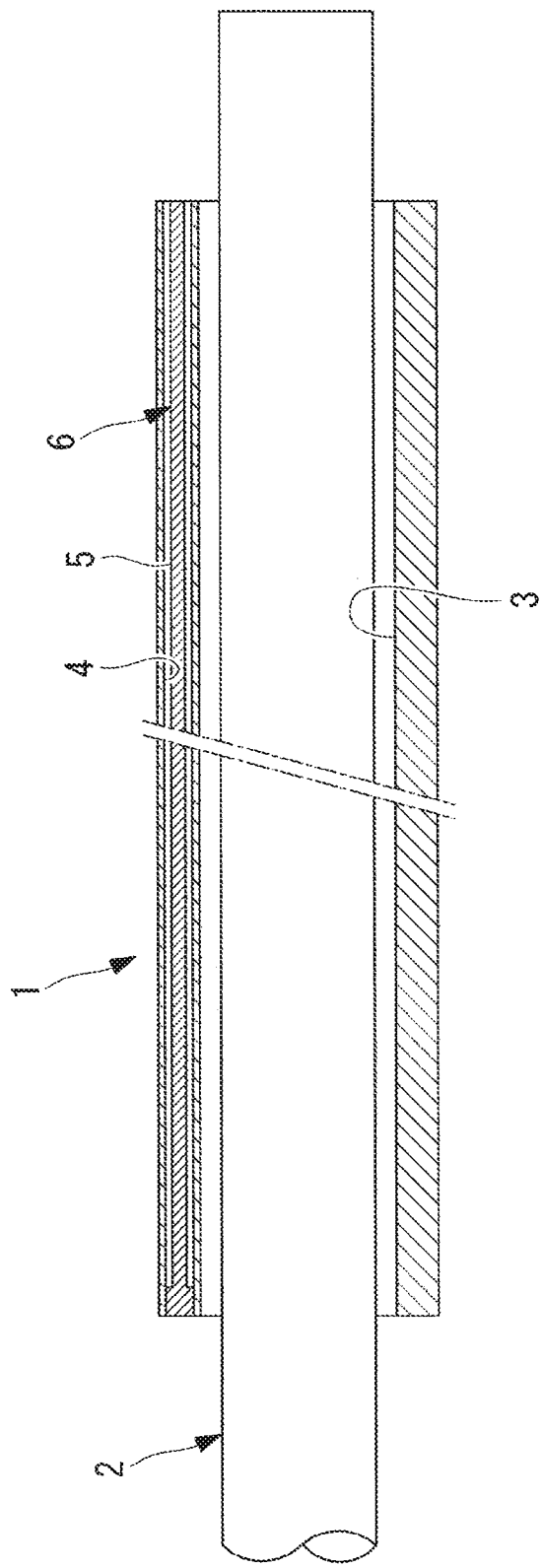
FIG. 1 is a longitudinal sectional view of an endoscope and an overtube used in a medical device insertion method according to one embodiment of the present invention.
Figure 2:
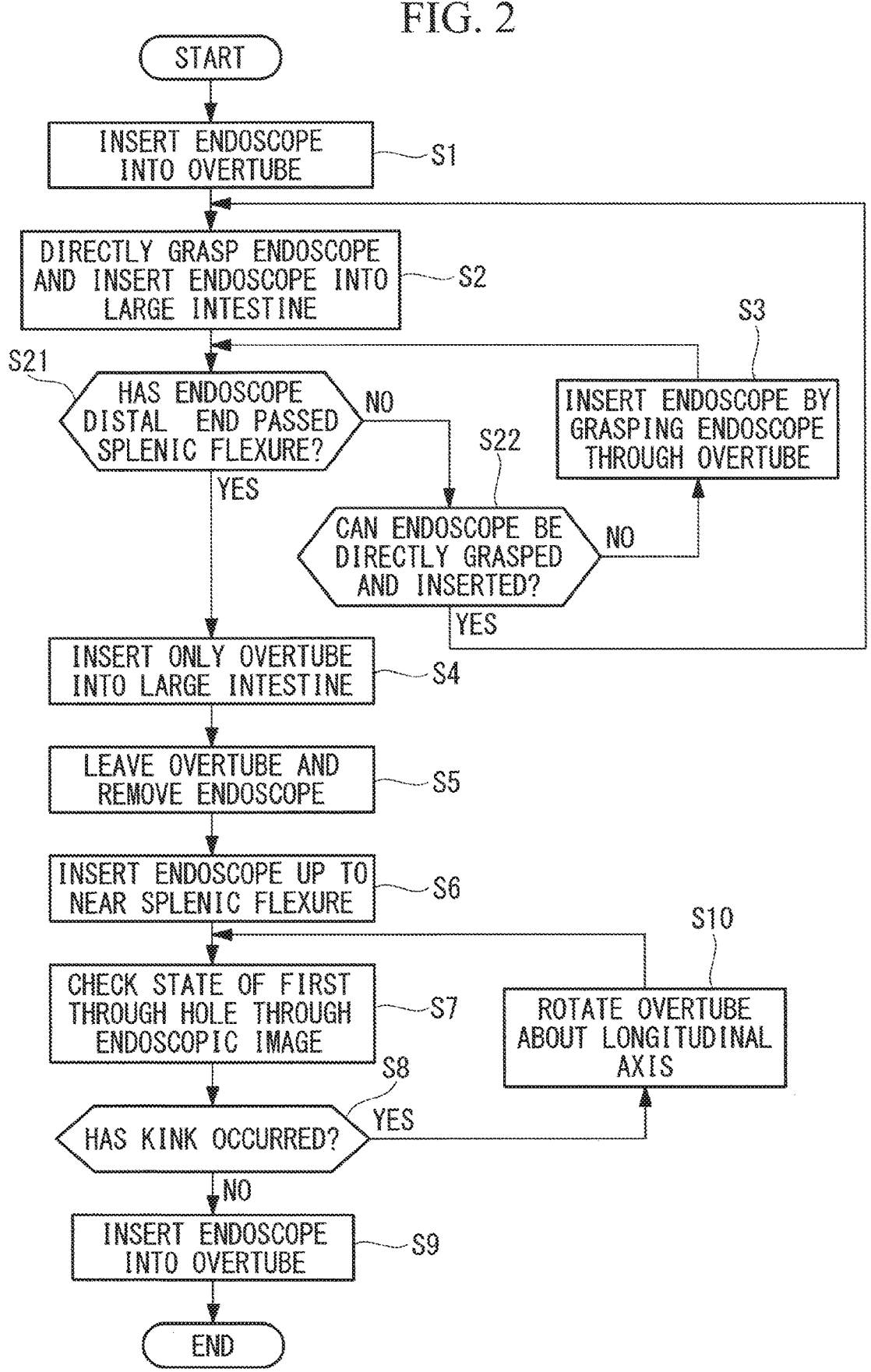
FIG. 2 is a flowchart illustrating a method for inserting the medical device illustrated in FIG. 1.

As illustrated in FIG. 1, the medical device insertion method of this embodiment relates to a method for inserting medical devices, such as an endoscope 2 and an overtube 1, into the large intestine X.

As illustrated in FIG. 1, the overtube 1 used in the medical device insertion method of this embodiment is composed of a flexible material, and has a large-diameter first through hole (inner hole) 3, which extends in the longitudinal axis direction and allows the endoscope 2 to pass therethrough, and a small-diameter second through hole 4 that runs parallel to the first through hole 3 and extends in the longitudinal axis direction. In the example illustrated in FIG. 1, the second through hole 4 extends throughout the entire length at one position in the circumferential direction, and, for example, a wire 5 composed of a metal material such as stainless steel is housed in the second through hole 4. In the example illustrated in FIG. 1, a reinforced region 6 reinforced by the wire 5 lies throughout the entire length.

The medical device insertion method includes a first step S1 performed outside the body of a patient, the step involving inserting the endoscope 2 into the first through hole 3 of the overtube 1; a second step S2 of directly grasping the endoscope 2 and inserting the endoscope 2 into the large intestine X; a third step S3 of inserting the endoscope 2 and the overtube 1 together into the large intestine X; and a fourth step S4 of inserting only the overtube 1 into the large intestine X.

Figure 3:
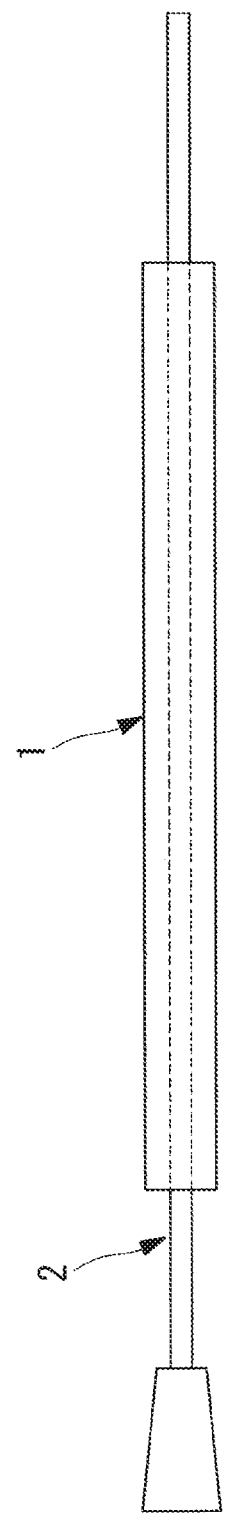
FIG. 3 is a schematic diagram illustrating a state in which the endoscope is inserted in the overtube in a first step of the medical device insertion method illustrated in FIG. 2.

As illustrated in FIG. 3, the first step S1 involves inserting the endoscope 2, which has been inserted from the proximal end side of the first through hole 3 of the overtube 1, until the endoscope 2 protrudes from the distal end of the overtube 1.

Figure 4:
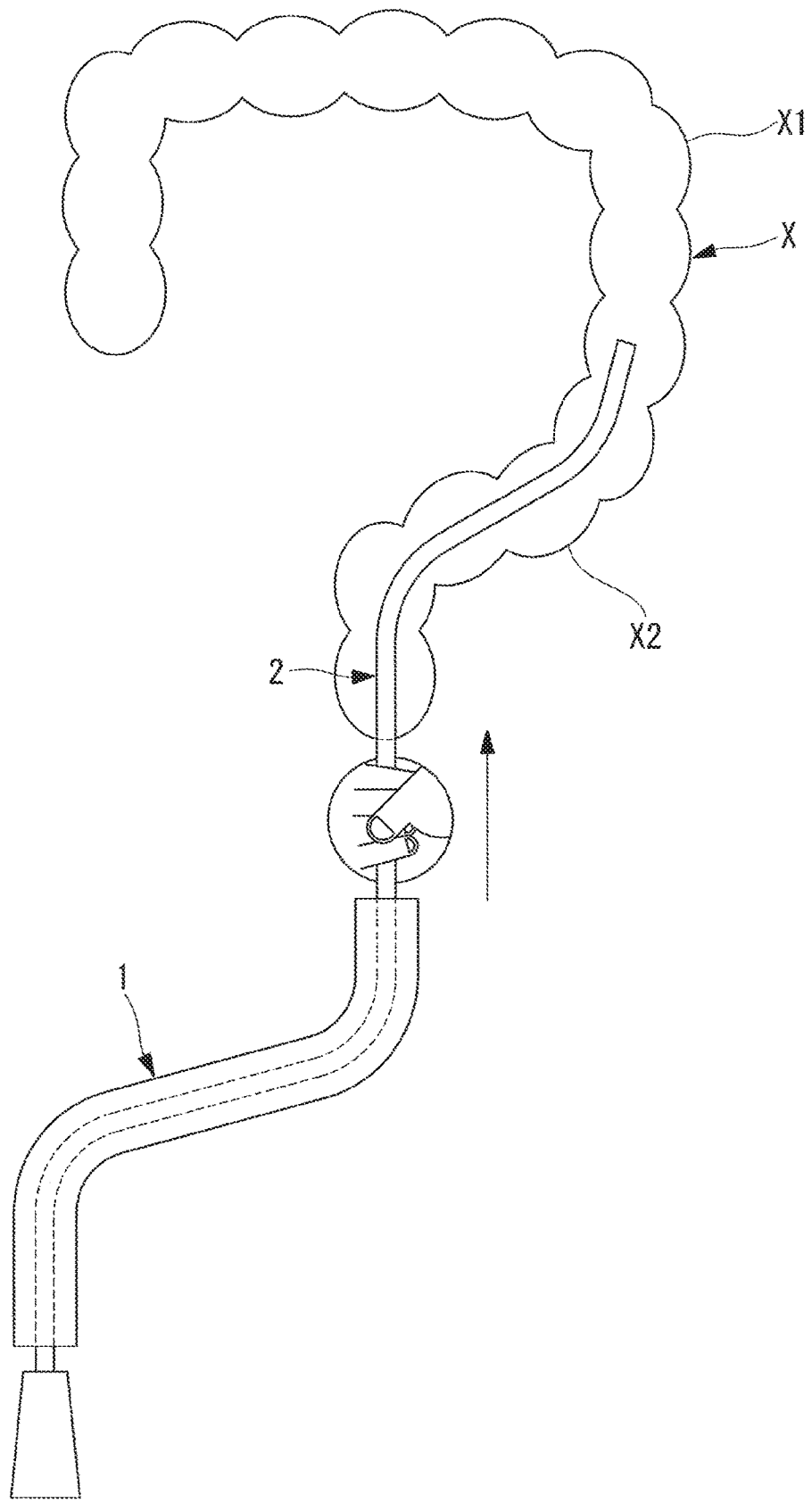
FIG. 4 is a schematic diagram illustrating a state in which only the endoscope is inserted into the large intestine in a second step of the medical device insertion method illustrated in FIG. 2.

As illustrated in FIG. 4, the second step S2 involves inserting only the endoscope 2 from the anus to the large intestine X while the operator directly grasps a part of the endoscope 2 protruding from the distal end of the overtube 1.

In the second step S2, the endoscope 2 is inserted until the distal end of the endoscope 2 reaches a position past the sigmoid colon X2 of the large intestine X. When the length of the endoscope 2 protruding from the distal end of the overtube 1 is sufficiently large, the distal end of the inserted endoscope 2 may reach a position past the splenic flexure X1 of the large intestine X by performing the second step S2, and whether or not the distal end of the endoscope 2 has passed the splenic flexure X1 is determined (step S21). When it is determined in step S21 that the distal end of the endoscope 2 has passed the splenic flexure X1, the fourth step S4 is performed without performing the third step S3.

When it is determined that the distal end has not passed the splenic flexure X1 in step S21, whether or not the endoscope 2 can be directly grasped and inserted is determined (step S22). If insertion by direct grasping is possible, the steps from the second step S2 onward are repeated.

When it is determined in the step S22 that the endoscope 2 cannot be directly grasped and inserted, the third step S3 is performed.

Figure 5:
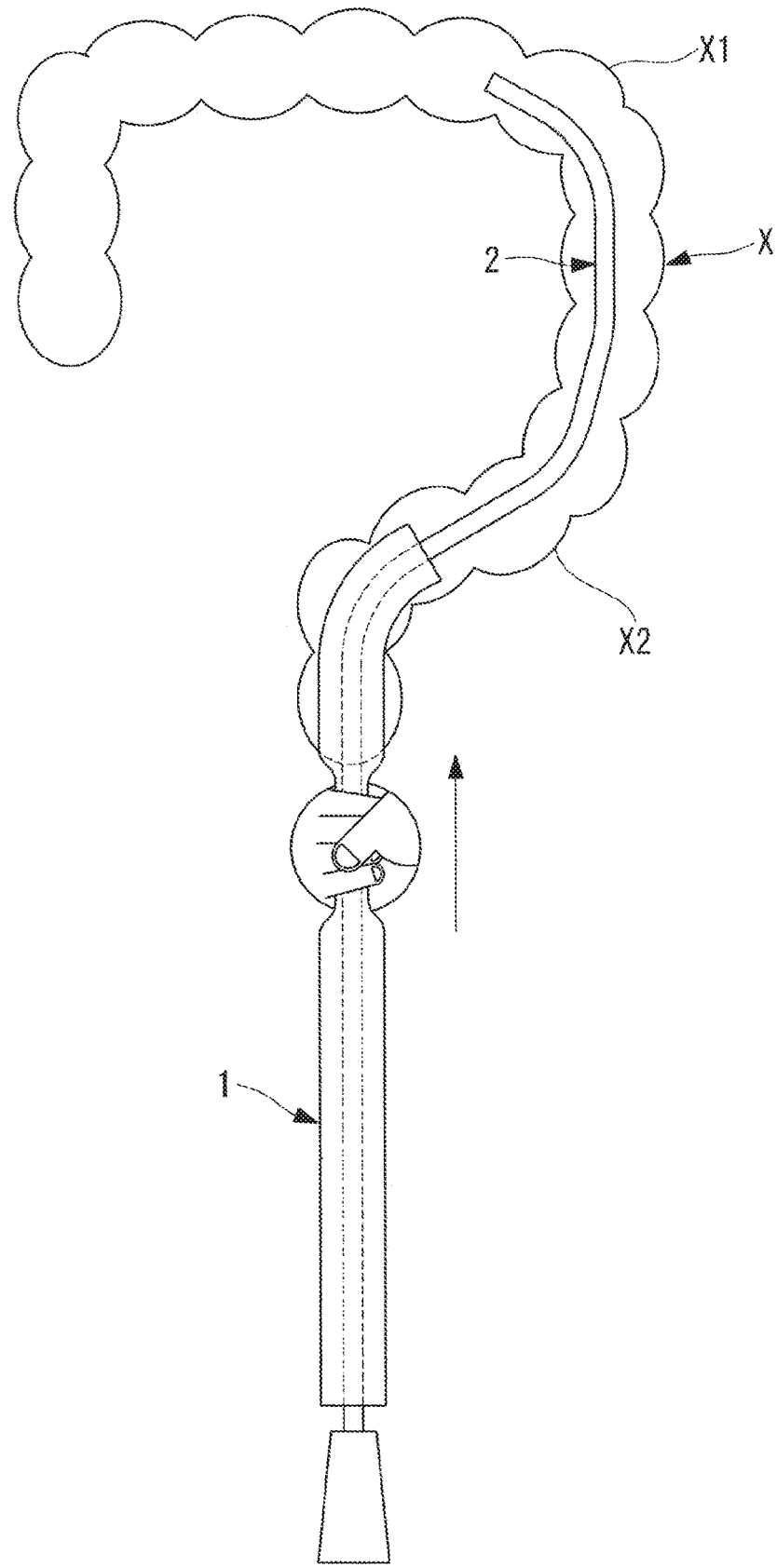
FIG. 5 is a schematic diagram illustrating a state in which the endoscope and the overtube are inserted into the large intestine in a third step of the medical device insertion method illustrated in FIG. 2.

As illustrated in FIG. 5, in the third step S3, the operator grasps the overtube 1 from the outer radial direction of the overtube 1 so as to compress the overtube 1 in the inner radial direction and cause the inner surface of the overtube 1 to closely attach to the outer circumferential surface of the endoscope 2. In other words, the operator grasps the endoscope 2 through the overtube 1. In this state, the grasped overtube 1 is advanced so as to insert the overtube 1 and the endoscope 2 together into the large intestine, and the steps from step S21 onward are repeated.

Although the wire 5 is built into the overtube 1, the wire 5 is placed only at one position in the circumferential direction; thus, the operator can grasp the overtube 1 and easily squash the overtube 1 in the radial direction. Thus, the operator can grasp the endoscope 2 as well as the overtube 1, and can apply a thrust force to the endoscope 2.

In step S21, when it is determined that the distal end of the endoscope 2 has passed the splenic flexure X1, the grasp force is released so as to allow the elastically deformed overtube 1 to regain its original form, and a thrust force is applied only to the overtube 1 so as to further insert only the overtube 1 into the large intestine X (fourth step S4).

Figure 6:
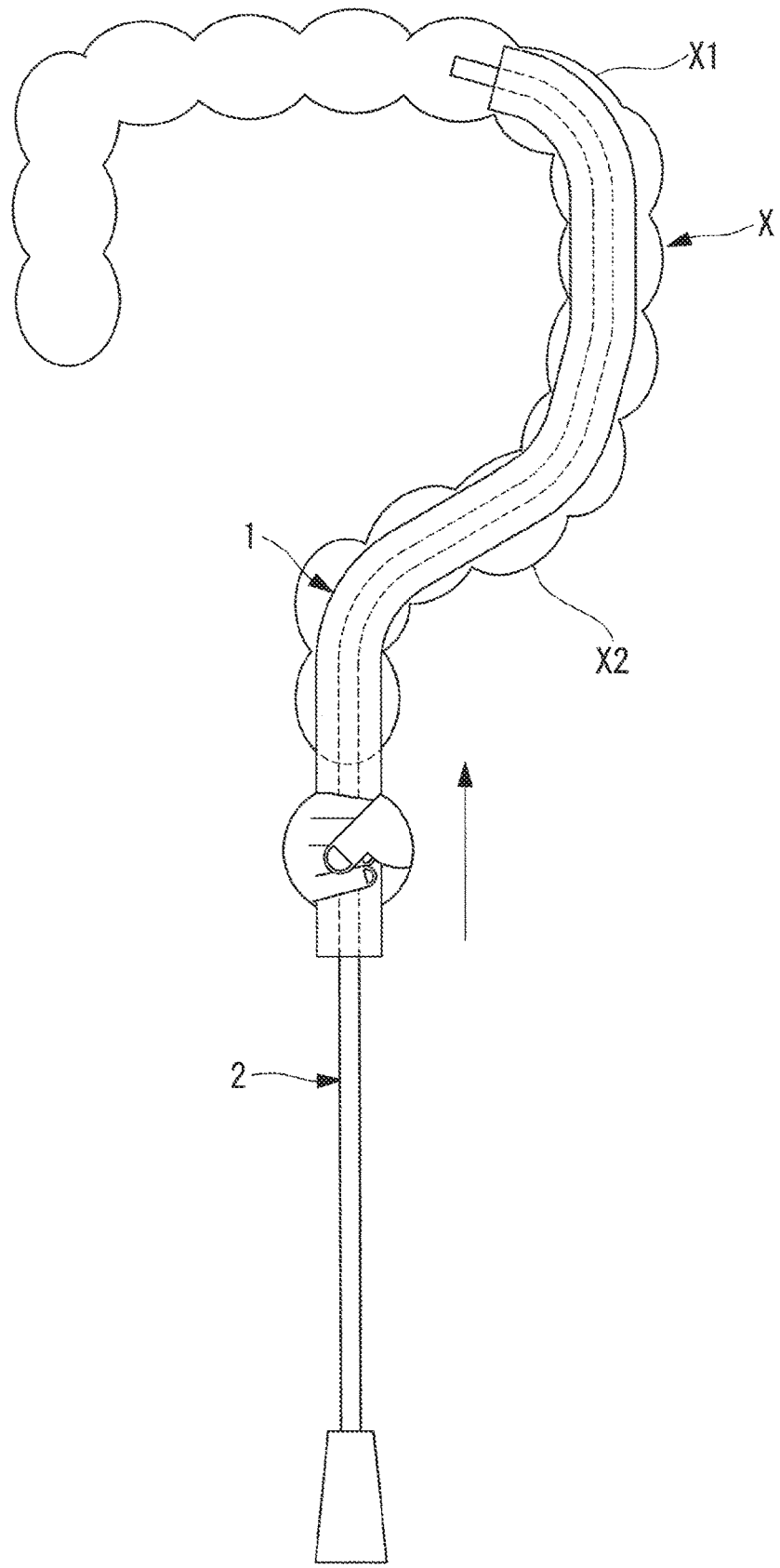
FIG. 6 is a schematic diagram illustrating a state in which only the overtube is advanced in the large intestine in a fourth step of the medical device insertion method illustrated in FIG. 2.

In the fourth step S4, as illustrated in FIG. 6, only the overtube 1 is inserted into the large intestine X until the distal end of the overtube 1 reaches a position past the splenic flexure X1.

Figure 7:
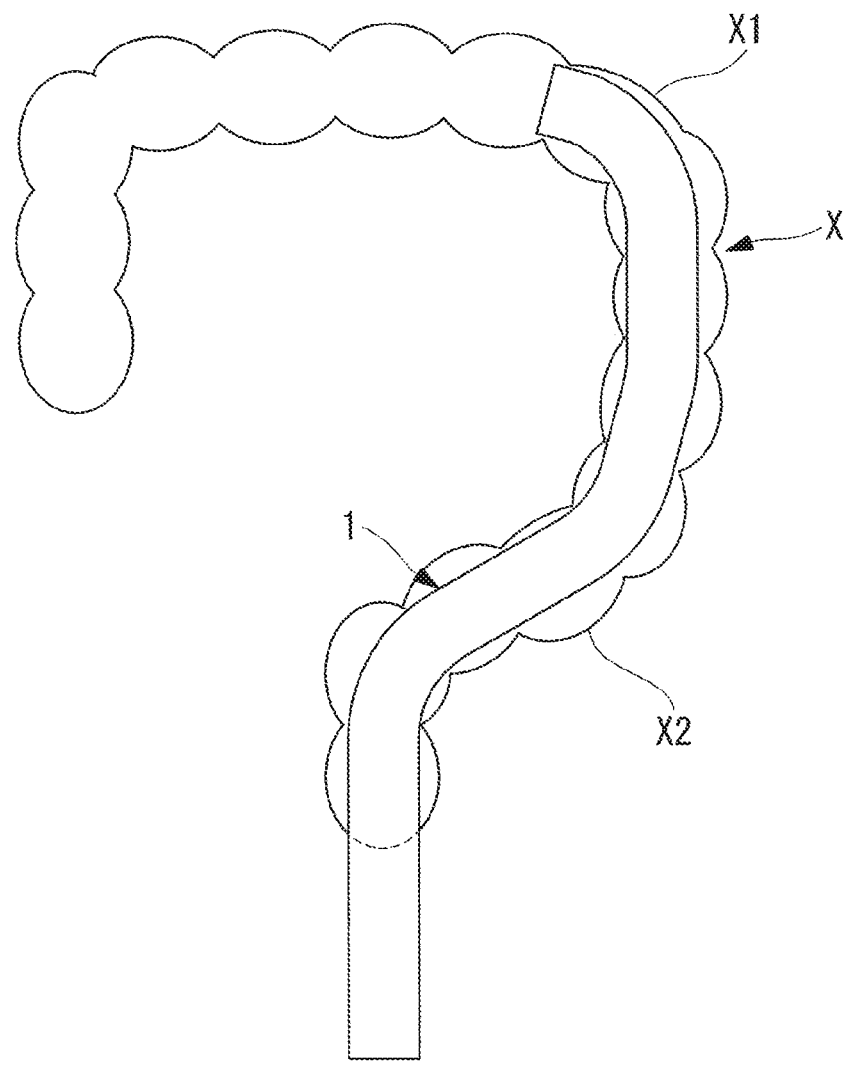
FIG. 7 is a schematic diagram illustrating a state in which the overtube is left while the endoscope is removed in the medical device insertion method illustrated in FIG. 2.

Subsequently, if for some reason the operator wishes to re-insert only the endoscope 2, as illustrated in FIG. 7, the overtube 1 is left in the large intestine X and only the endoscope 2 is removed (step S5).

Examples of such instances include replacing the endoscope 2 and removing contamination on the optical system at the distal end of the endoscope 2.

Figure 8:
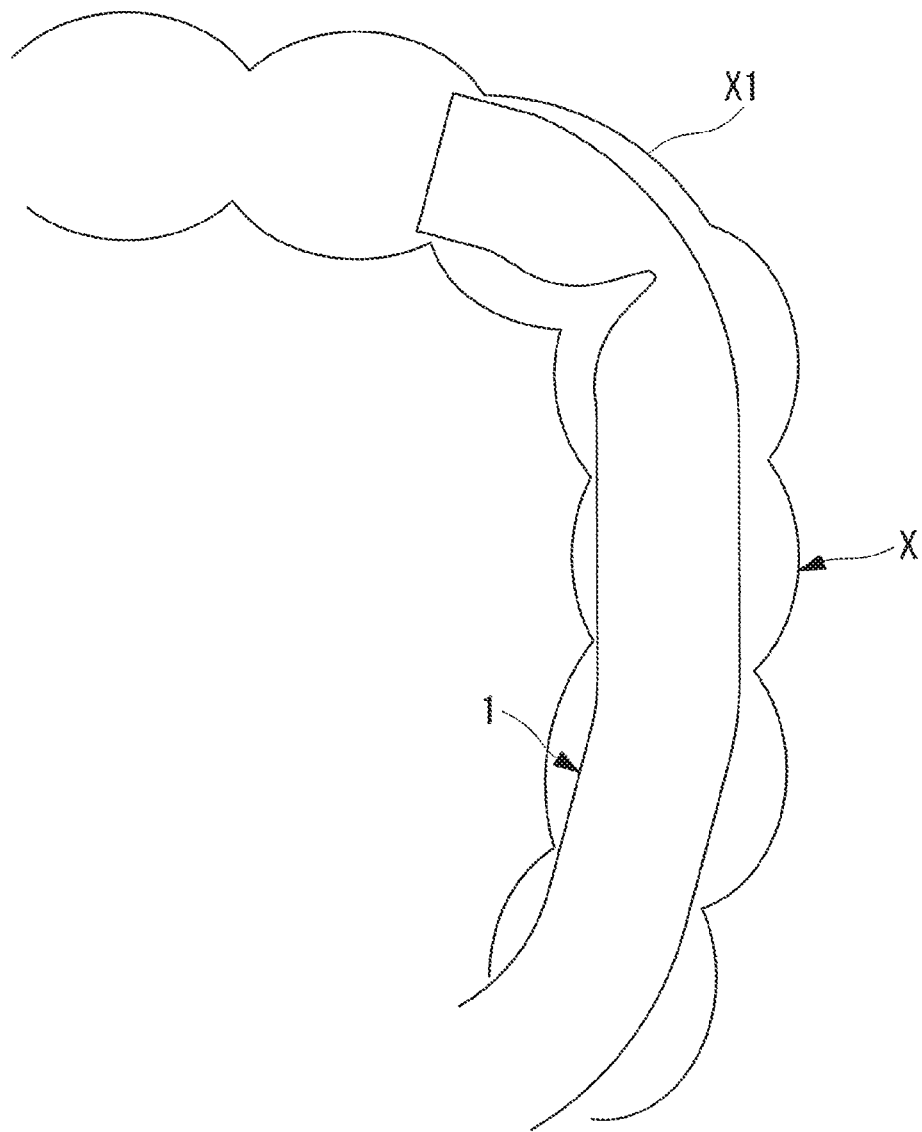
FIG. 8 is a schematic diagram illustrating a state in which the overtube is kinked in the state illustrated in FIG. 7.

As illustrated in FIG. 8, in such instances, when the endoscope 2 is to be re-inserted into the large intestine X by using the overtube 1 left in the large intestine X after the removal of the endoscope 2, the overtube 1, which is sharply bent in the splenic flexure X1, sometimes undergoes buckling, resulting in a kink.

Thus, the endoscope 2 is inserted into the overtube 1 up to a position near the splenic flexure X1 (step S6), and the endoscope 2 is actuated to check, through an endoscopic image, the state of the first through hole 3 of the overtube 1 at the splenic flexure X1, in other words, whether or not the first through hole 3 is squashed as a resulting of kinking (step S7).

The endoscopic image is checked to determine whether or not the overtube 1 is kinked (step S8), and if the overtube 1 is not kinked, the operation of inserting the endoscope 2 is directly performed (step S9). As a result, the endoscope 2 can be inserted up to a position where the distal end thereof passes the splenic flexure X1 and protrudes from the distal end of the overtube 1.

Figure 9:
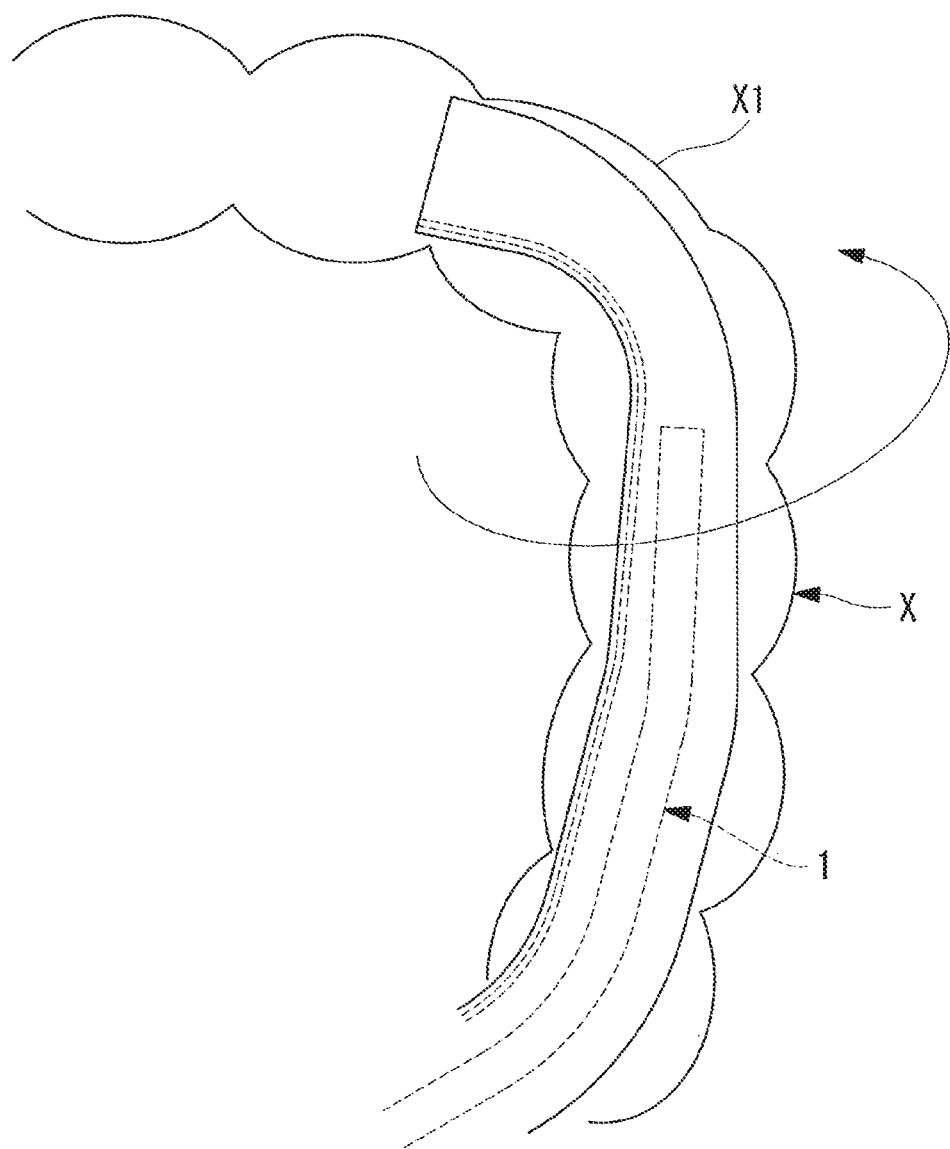
FIG. 9 is a schematic diagram illustrating the process of removing the kink illustrated in FIG. 8.

Meanwhile, if the overtube 1 is kinked, the operator grasps the part of the overtube 1 exposed outside the body and twists the part about the longitudinal axis so as to rotate, in the circumferential direction, the part that lies in the splenic flexure X1 (step S10). In this manner, as illustrated in FIG. 9, when the wire 5 is rotated to a position that lies on the inner circumferential side of the bend of the splenic flexure X1, kinking of the overtube 1 is removed, and the first through hole 3 is expanded. Thus, the process can return to step S9, and the endoscope 2 can be inserted.

As such, according to the medical device insertion method of this embodiment, after the endoscope 2 is directly grasped and inserted until the distal end of the endoscope 2 reaches a position near the splenic flexure X1, the endoscope 2 is advanced together with the overtube 1 by grasping the endoscope 2 through the overtube 1. Thus, there is an advantage in that a thrust force can be applied to the endoscope 2 at a position close to the anus so as to effectively carry out the insertion operation.

In other words, in the state in which the distal end of the overtube 1 is inserted in the large intestine X, it is possible to advance the endoscope 2 by directly grasping the endoscope 2 exposed on the proximal end side of the overtube 1; however, in such a case, the point at which the force is applied to the endoscope 2 is far from the anus, and thus, there is an issue that the endoscope 2 bends and the force is not smoothly transmitted. In contrast, when the endoscope 2 is grasped through the overtube 1 as in this embodiment, a force can be applied to the endoscope 2 at a position near the anus, and the applied force can be used in advancing the endoscope 2 without any loss.

Moreover, there is an advantage in that when only the overtube 1 is left in the large intestine X and a kink occurs in the overtube 1 in the splenic flexure X1, the kink can be resolved by merely rotating the overtube 1 about the longitudinal axis so as to enable re-insertion of the endoscope 2.

In other words, when an overtube 1 with a built-in coil tube is employed as the kink-resistant overtube 1, the overtube 1 cannot be compressed in the radial direction and the endoscope 2 cannot be grasped through the overtube 1; however, the medical device insertion method of this embodiment offers an advantage in that the endoscope 2 can be grasped through the overtube 1, while still allowing kinking can be easily removed.

When a kink occurs in the overtube 1, it is possible to remove the kink by partly withdrawing the overtube 1 until the distal end thereof comes to a position on the proximal side with respect to the splenic flexure X1; however, this increases the number of steps and complicates the operation. In contrast, the advantage of the medical device insertion method of this embodiment is that the method involves fewer steps and can be easily carried out.

Figure 10:
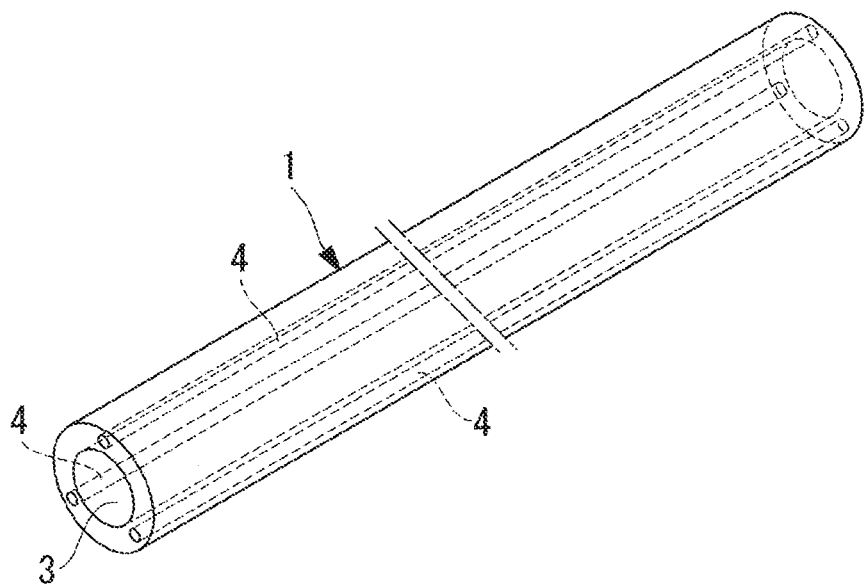
FIG. 10 is a perspective view of a modification of the overtube illustrated in FIG. 1.

Note that in this embodiment, an overtube in which the entirety of one wire 5 is housed inside the second through hole 4 is described as an example of the overtube 1; alternatively, the wire 5 may be bonded to the overtube 1 throughout the entire length or may be bonded only at one end. Moreover, as illustrated in FIG. 10, a plurality of wires may be arranged at intervals in the circumferential direction.

Figure 11:
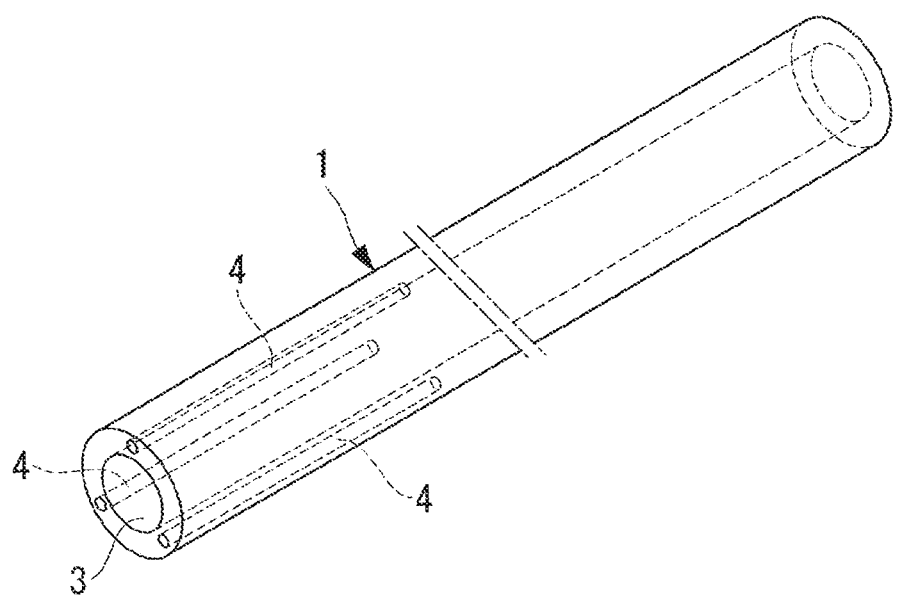
FIG. 11 is a perspective view of a modification of the overtube illustrated in FIG. 1.

Alternatively, as illustrated in FIG. 11, the wire 5 may be placed only near the distal end portion of the overtube 1 in the longitudinal direction. The wire 5 may be placed partially in a region that includes the range where the overtube 1 is caused to bend in the splenic flexure X1.

Alternatively, a tube equipped with a blade may be employed as the overtube 1 so as to transmit the torsional force applied outside the body and rotate the part that lies in the splenic flexure X1.

Alternatively, as illustrated in FIG. 12, a rigid holding portion 7 may be fixed to the proximal end portion in order to more smoothly apply the torsional force at the proximal end portion outside the body. In this case, the wire 5 is preferably fixed to the overtube 1 only at the distal end portion of the second through hole 4, and the proximal end side is preferably free and is preferably disposed inside the rigid holding portion 7.

According to this structure, damage to the overtube 1 inflicted by the free end portion of the wire 5 can be prevented.

REFERENCE SIGNS LIST 1 overtube
2 endoscope
3 first through hole (inner hole)
5 wire
6 reinforced region
X large intestine
X1 splenic flexure
X2 sigmoid colon

The invention claimed is:

1. A medical device insertion method for inserting an overtube and an endoscope into the large intestine, the overtube comprising a reinforced region in at least one part in a longitudinal axis direction, the reinforced region including a wire disposed in at least one part of an outer circumference of the overtube and disposed along the longitudinal axis direction, the method comprising:
   inserting the endoscope into the overtube until a distal end of the endoscope is positioned to protrude from a distal end of the overtube;
   grasping a part of the endoscope protruding from the distal end of the overtube and inserting the endoscope into the large intestine until the distal end of the endoscope is positioned between the splenic flexure and the sigmoid colon of the large intestine; and
   subsequent to the grasping, inserting the overtube together with the endoscope into the large intestine until the distal end of the endoscope is placed beyond the splenic flexure while grasping the overtube from an outer radial direction so as to deform the overtube in an inner radial direction until an inner surface of the overtube is pressed against an outer circumferential surface of the endoscope.

2. The medical device insertion method according to claim 1, further comprising, subsequent to the inserting of the overtube together with the endoscope, inserting the overtube into the large intestine until the reinforced region is placed in the splenic flexure.

3. The medical device insertion method according to claim 2, further comprising, subsequent to the inserting of the overtube into the large intestine until the reinforced region is placed in the splenic flexure, rotating the overtube about the longitudinal axis so as to resolve collapse of an inner hole of the overtube in the splenic flexure.

4. The medical device insertion method according to claim 3, wherein the rotating comprises, rotating the overtube about the longitudinal axis such that the wire is placed on an inner side of the bend of the splenic flexure.

5. The medical device insertion method according to claim 3, further comprising, before the rotating, checking a deformed state of the inner hole of the overtube in the splenic flexure with the endoscope.

\* \* \* \* \*